US009233063B2

(12) United States Patent
Lal et al.

(10) Patent No.: US 9,233,063 B2
(45) Date of Patent: Jan. 12, 2016

(54) POLYMERIC COMPOSITIONS FOR PERSONAL CARE PRODUCTS

(75) Inventors: Gauri Sankar Lal, Whitehall, PA (US); Richard Joseph Goddard, Fogelsville, PA (US); Mussarat Noor, Pittstown, NJ (US)

(73) Assignee: Air Products and Chemicals, Inc., Allentown, PA (US)

( * ) Notice: Subject to any disclaimer, the term of this patent is extended or adjusted under 35 U.S.C. 154(b) by 50 days.

(21) Appl. No.: 12/967,752

(22) Filed: Dec. 14, 2010

(65) Prior Publication Data

US 2011/0150794 A1 Jun. 23, 2011

Related U.S. Application Data

(60) Provisional application No. 61/287,529, filed on Dec. 17, 2009.

(51) Int. Cl.
*A61K 8/81* (2006.01)
*A61K 8/34* (2006.01)
*A61Q 15/00* (2006.01)
*A61Q 5/06* (2006.01)
*A61Q 17/04* (2006.01)
*A61Q 19/00* (2006.01)

(52) U.S. Cl.
CPC .............. *A61K 8/8152* (2013.01); *A61K 8/342* (2013.01); *A61Q 15/00* (2013.01); *A61Q 5/06* (2013.01); *A61Q 17/04* (2013.01); *A61Q 19/00* (2013.01)

(58) Field of Classification Search
CPC ................................................. A61K 8/8192
See application file for complete search history.

(56) References Cited

U.S. PATENT DOCUMENTS

| 3,937,811 | A | 2/1976 | Papantoniou et al. |
|---|---|---|---|
| 4,057,622 | A | 11/1977 | Hase et al. |
| 4,057,623 | A | 11/1977 | Hase et al. |
| 4,057,624 | A | 11/1977 | Hase et al. |
| 4,128,634 | A | 12/1978 | Hase et al. |
| 4,367,220 | A | 1/1983 | Boulogne et al. |
| 4,425,329 | A | 1/1984 | Tsutsumi et al. |
| 4,534,963 | A | 8/1985 | Gordon |
| 4,582,781 | A | 4/1986 | Chen et al. |
| 4,683,666 | A | 8/1987 | Igusa et al. |
| 4,792,444 | A | 12/1988 | Fukasawa et al. |
| 4,795,631 | A | 1/1989 | Sheehan |
| 4,830,855 | A | 5/1989 | Stewart |
| 5,057,580 | A | 10/1991 | Fock |
| 5,120,349 | A | 6/1992 | Stewart et al. |
| 5,156,911 | A | 10/1992 | Stewart |
| 5,318,995 | A | 6/1994 | Mondet et al. |
| 5,387,450 | A | 2/1995 | Stewart |
| 5,412,035 | A | 5/1995 | Schmitt et al. |
| 5,469,867 | A | 11/1995 | Schmitt |
| 5,470,884 | A | 11/1995 | Corless et al. |
| 5,518,712 | A | 5/1996 | Stewart |
| 5,519,063 | A | 5/1996 | Mondet et al. |
| 5,601,811 | A | 2/1997 | Gallagher et al. |
| 5,665,822 | A | 9/1997 | Bitler et al. |
| 5,736,125 | A | 4/1998 | Morawsky et al. |
| 5,752,926 | A | 5/1998 | Larson et al. |
| 5,783,302 | A | 7/1998 | Bitler et al. |
| 5,807,291 | A | 9/1998 | Larson et al. |
| 5,826,584 | A | 10/1998 | Schmitt |
| 5,849,318 | A | 12/1998 | Imai et al. |
| 5,879,718 | A | 3/1999 | Sebillote-Arnaud et al. |
| 5,959,009 | A | 9/1999 | Konik et al. |
| 5,989,295 | A | 11/1999 | de la Mettrie et al. |
| 6,199,318 | B1 | 3/2001 | Stewart et al. |
| 6,224,793 | B1 | 5/2001 | Hoffman et al. |
| 6,255,367 | B1 | 7/2001 | Bitler et al. |
| 6,306,411 | B1 | 10/2001 | Lezer |
| 6,342,237 | B1 | 1/2002 | Bara |
| 6,361,781 | B2 | 3/2002 | Lorant |
| 6,413,526 | B1 | 7/2002 | Bazin et al. |
| 6,464,969 | B2 | 10/2002 | De La Poterie et al. |
| 6,494,504 | B1 | 12/2002 | Fan |
| 6,540,984 | B2 | 4/2003 | Stewart et al. |
| 6,565,839 | B2 | 5/2003 | de la Poterie et al. |
| 6,569,409 | B1 | 5/2003 | Hansenne et al. |
| 6,793,940 | B2 | 9/2004 | Tournilhac et al. |
| 6,831,116 | B2 | 12/2004 | Bitler et al. |
| 6,946,518 | B2 | 9/2005 | de la Poterie |
| 6,949,504 | B2 | 9/2005 | Mondet et al. |

(Continued)

FOREIGN PATENT DOCUMENTS

| CN | 1568923 A | 1/2005 |
|---|---|---|
| EP | 1 466 579 A | 10/2004 |

(Continued)

OTHER PUBLICATIONS

GNPD, ID 364532, "Spray Solaire Sun Spray", 2013.
Porter, R. S. et al; On the Determination of the Melting Point of Semicrystalline Polymer by DSC,: Journal of Thermal Analysis, vol. 46 (1996) p. 871-878.
Rehberg, C. E. et al; "Preparation and Properties of the n-Alkyl Acrylates,"Eastern Regional Research Lab, Phila. PA; Jul. 1944; p. 1203-1206.
Jordan, Edmund et al; "Side-Chain Crystallinity. I. Heats of Fusion and Melting Transitions of Selected Homopolymers Having Long Side Chains;" Journal of Polymer Science, Part A-1; vol. 9 (1971) p. 1835-1852.
Overberbger, et al; "The Preparation and Polymerization of p-Alkylstyrenes. Effect of Structure of the Transition Temperatures of the Polymers;" Department of Chemistry, Institute of Polymer Research Polytechnic Institute of Brookly; Feb. 5, 2953; vol. 75; pp. 3326-3330.
Aharoni, Shaul M.; "Rigid Backbone Polymers. 2. Polymers. 2. Polyisocyanates and Their Liquid-Crystal Behavior;" Macromolecules; 1979 American Chemical Society; pp. 94-103.

(Continued)

*Primary Examiner* — Brian Gulledge
(74) *Attorney, Agent, or Firm* — Michael K. Boyer

(57) ABSTRACT

A polymeric composition is disclosed for use in personal care products. The composition is, at room temperature, a solid solution of a long-chain alcohol having ten to fifty carbon atoms and a polyalkyl[meth]acrylate polymer having some alkyl side chains pendant the ester group having ten to thirty carbon atoms and other alkyl side chains pendant the ester group having one to eight carbon atoms. The polymer can be formed by a transesterification reaction of a polyalkyl[meth]acrylate and the long chain alcohol in the presence of a catalyst.

34 Claims, No Drawings

(56) References Cited

U.S. PATENT DOCUMENTS

| | | | |
|---|---|---|---|
| 6,989,417 | B2 | 1/2006 | Bitler et al. |
| 7,090,420 | B2 | 8/2006 | De La Poterie et al. |
| 7,101,928 | B1 | 9/2006 | Bitler |
| 7,129,276 | B2 | 10/2006 | Ferrari |
| 7,255,870 | B2 | 8/2007 | Lennon et al. |
| 2001/0018484 | A1 | 8/2001 | Bitler et al. |
| 2002/0041857 | A1 | 4/2002 | De La Poterie et al. |
| 2002/0192251 | A1 | 12/2002 | Collin |
| 2002/0197220 | A1 | 12/2002 | Mondet et al. |
| 2003/0003154 | A1 | 1/2003 | De La Poterie |
| 2003/0147946 | A1 | 8/2003 | Stewart et al. |
| 2003/0215476 | A1 | 11/2003 | Cassin et al. |
| 2003/0235553 | A1 | 12/2003 | Lu et al. |
| 2004/0005279 | A1 | 1/2004 | Lorant et al. |
| 2004/0096473 | A1 | 5/2004 | Jager-Lezer |
| 2004/0136937 | A1 | 7/2004 | Cassin |
| 2004/0241112 | A1 | 12/2004 | Evison et al. |
| 2005/0013838 | A1 | 1/2005 | De La Poterie |
| 2005/0031547 | A1 | 2/2005 | Tamarkin et al. |
| 2005/0031565 | A1 | 2/2005 | Prud'Homme et al. |
| 2005/0031656 | A1 | 2/2005 | Pays et al. |
| 2005/0123493 | A1 | 6/2005 | Ferrari et al. |
| 2005/0131565 | A1 | 6/2005 | Blum et al. |
| 2005/0137117 | A1 | 6/2005 | Charbit |
| 2005/0142082 | A1 | 6/2005 | Ferrari |
| 2005/0169865 | A1 | 8/2005 | Parris |
| 2005/0175570 | A1 | 8/2005 | Inoue et al. |
| 2005/0205086 | A1 | 9/2005 | Tamarkin et al. |
| 2005/0261159 | A1 | 11/2005 | Parris et al. |
| 2005/0272615 | A1 | 12/2005 | Bitler |
| 2005/0272618 | A1* | 12/2005 | Bitler et al. .......... 508/469 |
| 2005/0276761 | A1* | 12/2005 | Gupta ................ 424/59 |
| 2006/0222606 | A1* | 10/2006 | Elliott et al. .......... 424/59 |
| 2007/0134192 | A1 | 6/2007 | Shimizu et al. |
| 2007/0189998 | A1* | 8/2007 | Nair et al. ............ 424/63 |
| 2008/0107615 | A1 | 5/2008 | Keene et al. |
| 2008/0194443 | A1 | 8/2008 | Stohr et al. |
| 2008/0269105 | A1 | 10/2008 | Taft et al. |
| 2008/0299058 | A1* | 12/2008 | Saito et al. .......... 424/59 |

FOREIGN PATENT DOCUMENTS

| | | |
|---|---|---|
| EP | 1466579 A1 | 10/2004 |
| FR | 2843025 A | 2/2004 |
| FR | 2846553 | 8/2008 |
| GB | 1480574 | 7/1997 |
| JP | 2283702 A2 | 11/1990 |
| JP | 4-39312 A | 2/1992 |
| JP | 9309818 | 12/1997 |
| JP | 2000-507273 A | 6/2000 |
| JP | 2000191473 | 7/2000 |
| JP | 2001507726 | 6/2001 |
| JP | 2003-040739 A2 | 2/2003 |
| JP | 2003-509539 A | 3/2003 |
| JP | 2003-212744 A2 | 7/2003 |
| JP | 2003-238348 A2 | 8/2003 |
| JP | 2004-315526 A2 | 11/2004 |
| JP | 2005-194220 A2 | 7/2005 |
| JP | 10053625 | 8/2008 |
| WO | 9307194 | 4/1993 |
| WO | 9825710 | 6/1998 |
| WO | 0004787 | 2/2000 |
| WO | 01/19333 A | 3/2001 |
| WO | 01/19333 A2 | 3/2001 |
| WO | 0134733 A1 | 5/2001 |
| WO | 03007898 A1 | 1/2003 |
| WO | 20040521 A1 | 12/2003 |
| WO | 2004041150 | 5/2004 |
| WO | 2004041220 | 5/2004 |
| WO | 2005123011 | 12/2005 |
| WO | 2007042679 A2 | 4/2007 |
| WO | 2007057448 A1 | 5/2007 |
| WO | 2007057451 A1 | 5/2007 |
| WO | 2009073192 A2 | 6/2009 |

OTHER PUBLICATIONS

O'Leary, K. A, et al.; "Physical properties of poly(n-alkyl acrylate) copolymers. Part 1. Crystalline/crystalline combinations;" Polymer 47 (2006) pp. 1226-1244, et al.

O'Leary, K. A., et al; "Physical properties of poly(n-alkyl acrylate) copolymers. Part 2. Crystalline/non-crystallin combinations;" Polymer 47 (2006) pp. 1245-1258.

Rehbert, C. E. et al; "Preparation and Properties of the n-Alkyl Acrylates;" The Eastern Regional Research Laboratory, Philadelphia, PA. vol. 66, Jul. 1944; pp. 1203-1207.

Port, Williams S., et al.; "Polymerizable Derivatives of Long Chain Fatty Acids. VII Copolymerization of Vinyl Acetate with Some Long-Chain Vinyl Esters;" Journal of Polymer Science; vol. IX. No. 6; pp. 493-502.

Greenberg, Sidney A., et al; "Side Chain Crystallization of n-Alkyl Polymethacrylates and Polyacrylates;" The Institute of Polymer Research, Polytechnic Institute of Brooklyn; 1954; vol. 76; pp. 6280-6285.

Jordon, Jr., Edmund F.; et al; "Copolymers of Vinyl Alcohol and Vinyl Stearate;" Journal of Polymer Science; vol. XXXII, (1958) pp. 33-46.

Jordon, Jr., Edmund F., et al; "Polymerizable Derivatives of Long-chain alcohols. II. Reactivity Ratios for the Copolymerization of Some Alkyl Acrylates;" Journal of Applied Polymer Science; vol. IV, Issue No. 11 (1960); pp. 203-206.

Jordon, Jr., Edmund F., et al; "Mechanical Properties and Transition Temperatures for Copolymers of N-n-Alklylacrylamides and Acrylonitrile;" Journal of Polymer Science: Part A-2; vol. 4 (1966); pp. 975-996.

Jordan, Jr., Edmund F., et al; "Chain Transfer Constants for vinyl Monomers Polymerized in Methyl Oleate and Methyl Stearate;" Journal of Polymer Science: Part A-1; vol. 7. (1969) pp. 2605-2620.

Jordon, Jr., Edmund F., et al; "Reactivity Ratios and Copolymerization Parameters for Copolymers Incorporating n-Octadecyl Acrylate and N-n-Octadecylacrylamide;" Journal of Polymer Science: Part A-1; vol. 8; (1970) pp. 3113-3121.

Jordon, Jr., Edmund F., et al; "Side-Chain Crystallinity. IV. Mechanical Properties and Transition Temperatures of Copolymers of Methyl Methacrylate with Higher n-Alkyl Acrylates and N-n-Alkylacrylamides;" Journal of Polymer Science Part A-2; vol. 10 (1972) pp.

Jordan, Jr., Edmund F., et al; "Side-Chain Crystallinity. II. Heats of Fusion and Melting Transitions on Selected Copolymers Incorporating n-Octadecyl Acrylate or Vinyl Stearate;" Journal of Polymer Science: vol. 9; (1971) pp. 3349-3365.

Jordan, Jr., Edmund F., et al; "Side-Chain Crystallinity. III. Influence of Side-Chain Crystallinity on the Glass Transition Temperatures of Selected Copolymers Incorporating n-Octadecyl Acrylate or Vinyl Stearate;" Journal of Polymer Science: Part A-1; vol. 9 (1971) pp. 3367-3378.

Plate, N. A., et al; "Comb-Like Polymers. Structure and Properties;" Polymer Science; Macromolecular Reviews, vol. 7, (1974) pp. 117-253.

Stevens, et al, U.S. Appl. No. 60/799,616, filed May 11, 2006.

Noor, et al, U.S. Appl. No. 60/900,847, filed Feb. 12, 2007.

Noor, et al, U.S. Appl. No. 11/747,261, filed Nov. 14, 2007.

Widmer, All Day 20: http://www.louis-widmer.fi/0021wd_02020602_en.htm.

Cosmetics Bench Reference Directory (CBT). Intelimer 8600 Emulsion Polymer/ C8-22 alkyl acrylate/methacrylic acid cross polymer. http://dir.cosmeticsandtoiletries.com/detail/tradeName.html?id=18913.

Eyelashes: http://www.liveindia.com/fashion/b5a.html.

Greene et al: Side-Chain Crystallizable Polymers for Temperature-Activated Controlled Release; ACS Symposium Series; American Chemical Society (1993) pp. 244-256.

Unilin Alcohols, Baker Hughes; Release BPPD 30-1 (2001).

Landec Business Wire; Feb. 18, 2004 pp. 1 and 2.

* cited by examiner

POLYMERIC COMPOSITIONS FOR PERSONAL CARE PRODUCTS

CROSS-REFERENCE TO RELATED APPLICATIONS

This Application claims the benefit of Provisional U.S. Application No. 61/287,529, filed on Dec. 17, 2009. The disclosure of Application No. 61/287,529 is hereby incorporated by reference.

BACKGROUND OF THE INVENTION

The present disclosure relates generally to the field of polymeric compositions for use in personal care products and more particularly to polymeric compositions that include side-chain crystalline polymers derived from acrylic acid esters.

Polymeric thickeners are sometimes used for oil-containing compositions used for cosmetic and other personal care products. In some cases, these compositions may contain side-chain crystalline polymers uniformly dispersed in the oil. A broad range of side chain crystalline polymers can be used to thicken oils in such cases and generally contain lipophilic groups such as long alkyl chains. These polymers can be used to supplement, or in place of, surface active agents previously used in these kinds of formulations. One such group of materials includes side-chain crystalline polymers derived from acrylic acid esters bearing linear side-chains containing 10-50 carbon atoms (e.g., 10 to 30 carbon atoms). Such polymers have also been used for the encapsulation of active materials, such as catalysts, within the polymer matrix. An example of this class of polymers is the Intelimer® compounds developed by Landec Corporation. Side chain crystalline polymers are further discussed in U.S. Pat. Nos. 6,199,318 and 6,989,417, which are hereby incorporated by reference in their entirety.

The Intelimer compounds and other known side-chain crystalline polymers derived from acrylic acid esters bearing linear side-chains are primarily homopolymers of large (alkyl)acrylic monomers created by free radical polymerization. Free radical polymerization has the drawback in that large (alkyl)acrylic monomers are often difficult and time consuming to procure and process. Other methods for creating side-chain polymers are described in WO 01/48032, US Pub No 20040250465 and U.S. Pat. No. 6,265,360, also incorporated by reference, which relate to polymers used in fuel compositions.

Exemplary embodiments of the present invention overcome these and other drawbacks by providing compositions that are easier to procure and process and still have desirable characteristics for use in personal care products.

BRIEF SUMMARY OF THE INVENTION

According to an exemplary embodiment, a composition comprises an alcohol having the composition R'OH and a polyalkyl[meth]acrylate having a repeating unit:

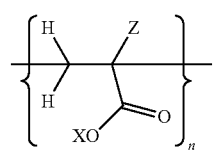

Z is hydrogen or a methyl group; X, independently for each repeating unit, is R or R'; R is an alkyl group having 1 to 8 carbon atoms (e.g., 1 to 4 carbon atoms); R' is an alkyl group having 10 to 50 carbon atoms (and typically having 10 to 30 carbon atoms); and n is an integer such that the composition has a weight average molecular weight in the range of about 10,000 to about 250,000 g/mol (e.g., 40,000 to 140,000 g/mol). Repeating units of the polyalkyl[meth]acrylate in which X is R' make up about 60 to about 99.5 mol % of the total number of repeating units n and repeating units of the polyalkyl[meth]acrylate in which X is R make up about 0.5 to about 40 mol % of the total number of repeating units n. R'OH is present in the range of about 0.5 to about 40 mol % relative to the total number of repeating units n.

According to another exemplary embodiment, a personal care product is disclosed comprising a cosmetic base media selected from the group consisting of cosmetic oil, water, alcohol and combinations thereof and about 0.1% to about 20% by weight of a compound comprising or consisting essentially of the alcohol/polyalkyl[meth]acrylate composition described above. According to yet another exemplary embodiment, a method of making such a composition is also disclosed that comprises:

(a) reacting an alcohol with a polyalkyl[meth]acrylate having a repeating unit A, optionally in a solvent, in the presence of a catalyst to form a substituted alcohol and a substituted polyalkyl[meth]acrylate having a repeating unit B according to the following reaction scheme:

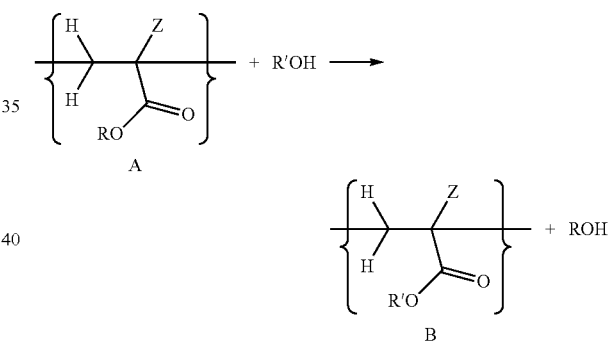

wherein
Z is hydrogen or a methyl group,
R is a straight chain alkyl group having 1 to 8 carbon atoms,
R' is a straight chain alkyl group having 10 to 50 carbon atoms (e.g., 10 to 30 carbon atoms), and
wherein the substituted polyalkyl[meth]acrylate is a random copolymer of
repeating units A and B; and (b) removing the substituted alcohol ROH and any solvent from the reaction product to form a composition consisting essentially of the alcohol R'OH and the substituted polyalkyl[meth]acrylate, wherein the composition formed includes a polyalkyl[meth]acrylate in which about 60 to about 99.5 mol % of the repeating units are repeating unit B, about 0.5 to about 40 mol % of the repeating units are repeating unit A, and the alcohol R'OH is present in the range of about 0.5 to about 40 mol % relative to the total number of repeating units A and B, the composition having a weight average molecular weight in the range of about 10,000 to about 250,000 g/mol.

Compositions and methods in accordance with exemplary embodiments of the invention are useful in conjunction with cosmetic and other personal care applications and may be used as a thickening agent as well as a vehicle for encapsulation, deposition and delivery of chemical actives in such applications.

Other features and advantages of the present invention will be apparent from the following more detailed description of exemplary embodiments that illustrate, by way of example, the principles of the invention.

DETAILED DESCRIPTION OF THE INVENTION

Described herein are polymeric compositions which can be achieved through the transesterification reaction of a polyalkyl[meth]acrylate polymer in the presence of a long chain alcohol. As shown in Equation (1), the alcohol is reacted with a repeating unit A of a polyalkyl[meth]acrylate in the presence of a catalyst:

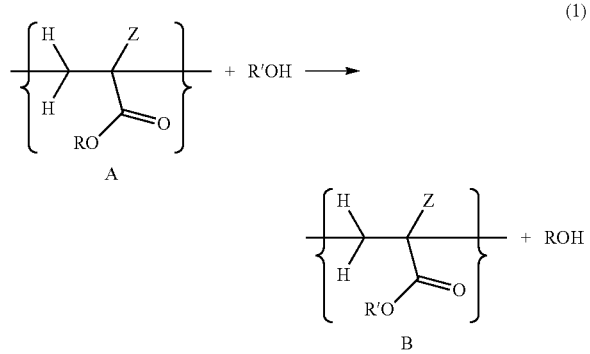

in which Z is hydrogen or a methyl group depending on whether the particular repeating unit is an acrylate or methacrylate.

The alkyl group R pendant to the ester in the repeating unit A of the polyalkyl[meth]acrylate is substituted with the alkyl group R' of the long chain alcohol R'OH. This results in formation of a substituted polyalkyl[meth]acrylate having a repeating unit B, while the alkyl group R of the repeating unit A of the initial polyalkyl[meth]acrylate forms a substituted alcohol ROH.

The alkyl group R is a linear short-chain group that has between one and eight carbon atoms. More typically, the short chain alkyl group R has between one and four carbon atoms.

The initial polyalkyl[meth]acrylate polymer to be reacted may have repeating unit A as the only repeating unit of the polymer. The polymer may thus be a homopolymer of any one of a methyl[meth]acrylate, ethyl[meth]acrylate, propyl[meth]acrylate, butyl[meth]acrylate, pentyl[meth]acrylate, hexyl[meth]acrylate, heptyl[meth]acrylate or octyl[meth]acrylate repeating unit or it may be a copolymer of two or more of these [meth]acrylate repeating units. In one embodiment, the initial polymer to be reacted is poly(methyl acrylate) homopolymer.

It will be appreciated, however that the initial polyalkyl [meth]acrylate polymer to be reacted may also be a block or random copolymer of an acrylate or methacrylate having a repeating unit A along with one or more other types of repeating units, such as those formed by non-acrylic monomers. Optional other types of repeating units may include functional groups that are not reactive during the transesterification, and/or functional groups that are reactive during the transesterification, the latter potentially resulting in a cross-polymer. Examples of other types of repeating units that may be included in the initial polyalkyl[meth]acrylate polymer having a repeating unit A include N,N-dialkylamino[meth]acrylamides, N-alkyl[meth]acrylamides, N,N-dialkyl[meth]acrylamides, acrylamide, methacrylamide, N-methylacrylamide, N-methylmethacrylamide, N,N-dimethylacrylamide, N,N-dimethylmethacrylamide, N,N-diethylacrylamide, diacetoneacrylamide, N,N-dimethylaminopropylacrylamide, N-butoxymethylacrylamide, N-ethoxymethylacrylamide, N-n-butylacrylamide, N-tertbutylacrylamide, N-isopropylacrylamide, N-methylolacrylamide, N-methoxymethylacrylamide, N-ethylacrylamide, N-(3-methoxypropyl)acrylamide, N-n-propylacrylamide, N-trimethylbutylacrylamide, N-2-ethylhexylacrylamide, N-isooctylacrylamide, N-acetylmethacrylamide, N-butoxymethylmethacrylamide, N,N-dibutylaminopropylmethacrylamide, N-2-ethylhexylmethacrylamide, N,N-dimethylaminopropylmethacrylamide, N,N-diethylmethacrylamide, N-(2,2-dimethoxyethyl)methacrylamide, N,N-dimethylaminoethylmethacrylamide, N-ethylmethacrylamide, N-hydroxyethylmethacrylamide, N-(3-hydroxypropyl)methacrylamide, N-methoxymethylmethacrylamide, N-(3-methoxypropyl)methacrylamide, N,N-diallylmethacrylamide, N-methylolmethacrylamide, 2-methacryloxy-N-ethylmorpholine, [meth]acrylic acid, itaconic acid, crotonic acid, citraconic acid, maleic acid, methyl maleate, butyl maleate, acrylamidomethylpropane sulfonic acid, fumaric acid, mesaconic acid, glutaconic acid, maleic anhydride, and itaconic anhydride, hydroxyethyl[meth]acrylamide, hydroxypropyl[meth]acrylamide, hydroxybutyl [meth]acrylamide, hydroxyhexyl[meth]acrylamide, vinyl alcohol (from vinyl acetate), vinylpyrrolidinone, N-vinylformamide, vinyl esters, alkylvinyl ethers, vinyl amides, styrene, p-alkyl styrenes and mixtures thereof.

The long chain alcohol R'OH has an alkyl group R' having between ten and fifty carbon atoms (e.g., between ten and thirty), that is substituted for the short chain alkyl group R of the polymer during the transesterification reaction. In one embodiment, R' is a straight chain alkyl group having between 16 and 22 carbon atoms; typically R' is a stearyl (i.e. 1-octadecyl) or behenyl (i.e. 1-docosanyl) group. It will be appreciated that R' need not be the same alkyl group in every case, but that multiple different long chain alcohols of the formula R'OH may be present in the reaction mixture. For example, each of stearyl and behenyl alcohol may be present in the reaction mixture such that some of the short-chain alkyl groups R of repeating unit A are substituted with a stearyl group, while others are substituted with a behenyl group.

The molar ratio of repeating units A to long chain alcohol R'OH in the initial reaction mixture may range from about 0.6:1 to about 1:0.6. In some embodiments, the molar ratio may range from about 0.9:1 to about 1:0.9, and in still other embodiments, the molar ratio of the initial reaction mixture may be about 1:1.

It will be appreciated that in addition to the long chain alcohol R'OH that can react to form the repeating unit B, other alcohol groups may be included in the tranesterification reaction to substitute the alkyl group R, with the result that a copolymer of repeating units A and B and other repeating units is formed. Other alcohol groups that may be included may include mono-alcohols, glycols and triols, with cross-polymers potentially formed when polyols are included. Examples include polyethers, alkyl polyethers, poly(alkoxylated) alcohols, glycols, trimethylolpropane, glycerine, pentaerythritol, 1,2,5-pentanetriol, 1,2,6-hexanetriol, sorbitol, glycol ethers, hydroxyl-terminated oligomers, hydroxyl-terminated polydimethylsiloxane, hydroxyl-terminated siloxanes, hydroxyl-terminated organosiloxanes, hydroxyl-terminated polyethers, hydroxyl-terminated lactones, hydroxyl-terminated polybutadiene, hydroxyl-terminated polyisoprene, and mixtures thereof.

The reaction occurs in the presence of a catalyst, which may be any suitable catalyst for conducting a transesterification reaction. Exemplary catalysts include mineral acids, sulfonic acids, fluoroacids (such as trifluoroacetic acid) as well as mixtures of these. Sulfonic acid catalysts may be represented by the formula R"SO$_3$H, where R" is a hydrocarbyl group of 1 to about 25 carbon atoms, such as methanesulfonic acid. Other exemplary catalysts include solid acids such as Nafion® resins, Amberlyst® resins, zeolites, molecular sieves and acidified clay. Isopropyl and butyl titanates are also useful. Still other catalysts may also be used, such as alkali metal oxides, hydroxides or alkoxides, particularly those of potassium or sodium, as well as oxides, alkyls, carboxylates, halides and alkoxides of transition metals such as tin, zinc, zirconium, titanium, aluminum and manganese, such as butyl tin oxide, Ti(OR''')$_4$ and Ti(R''')$_4$, in which R''' is an alkyl group.

As previously discussed, during the transesterification reaction of Equation 1, some of the short chain alkyl groups R in the repeating units A are replaced with the long chain alkyl groups R' of the alcohol, while the supplanted short chain alkyl units R form short chain alcohols ROH.

Some of the substituted (i.e. short chain) alcohol compound ROH that is formed during the reaction may be removed from the reaction mixture while the reaction is ongoing. This can help drive the substitution reaction and increase the number of repeating units in the polyalkyl[meth]acrylate that are substituted with the R' alkyl group. Any ROH not removed during the reaction is typically removed at the conclusion of the reaction to yield a solid reaction product that is a solid solution of the substituted polyalkyl[meth]acrylate and the long chain alcohol R'OH.

The reaction may be carried out in the presence of solvent, which can be any suitable organic solvent. As described and shown in Equation 1, as the reaction proceeds, short chain alcohols (ROH) are formed as the short chain alkyl groups R of the initial polyalkyl[meth]acrylate are replaced by the long chain alkyl group R' of the long chain alcohol R'OH. Thus, a particularly suitable organic solvent may include those that form an azeotrope with the short chain alkyl alcohols (ROH). In the cases where R is an alkyl group having one to four carbons, toluene is a desirable solvent; xylene may also be used. Other suitable solvents may include hydrocarbons, such as decane; ethers, such as diglyme; and nitriles, such as acetonitriles, all by way of example only.

In one embodiment, the substituted alcohol ROH can be removed by removing solvent from the reaction mixture or the reaction product by any suitable measure, for example, including vacuum distillation. Because the reaction is typically carried out while heating under reflux, the substituted alcohol and/or solvent can also be removed from the reflux stream, replacing the lost alcohol/solvent with fresh solvent.

Although the short chain alcohol ROH is removed from the composition either during or after the reaction, the reaction generally reaches equilibrium without all of the long chain alcohol molecules R'OH being consumed, even when excess long chain alcohol is present. As a result, in most cases not all of the repeating units A of the initial polyalkyl[meth]acrylate will become substituted.

Thus, the substituted polyalkyl[meth]acrylate that contains the repeating units B formed by the reaction will usually be a copolymer of repeating units A and B, with those repeating units randomly positioned along the polymer chain. That is, following the reaction the polyalkyl[meth]acrylate will contain the repeating unit

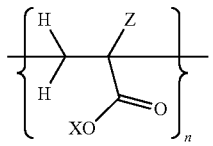

in which Z is hydrogen or a methyl group; n is an integer corresponding to the total number of these repeating units in the polymer chain; and X, independently, is either R or R'.

It will be appreciated that because the reaction is a substitution reaction involving an already existing polymer, the reaction does not generally cause any change in the number of chains being formed or broken in the initial versus the substituted polyalkyl[meth]acrylate. Thus, each polymer chain will have approximately n repeating units before and after the reaction, although the molecular weight of the substituted polyalkyl[meth]acrylate will be greater than that of the initial polymer as a result of the greater molecular mass of the alkyl substituent groups R'.

Following removal of the short chain alcohol ROH and solvent from the reaction mixture, a solid product is obtained of a composition that includes the substituted polyalkyl [meth]acrylate and the long-chain alcohol R'OH. The resulting composition of the substituted polyalkyl[meth]acrylate and the long chain alcohol R'OH has a weight average molecular weight in the range of about 10,000 to about 250,000 g/mol; in one embodiment, the molecular weight is about 40,000 to about 140,000 g/mol. It will be appreciated, however, that the particular molecular weight desired may depend on the particular end use for the which the composition is to be employed. The molecular weight can be controlled through the ratio of the reactants employed, as well as through the selection of the molecular weight of the initial polyalkyl [meth]acrylate.

Repeating units of the substituted polyalkyl[meth]acrylate containing the long-chain alkyl group (i.e. repeating unit B) make up about 60 to about 99.5 mol % of the total number of repeating units n (i.e., A+B), while repeating units of the substituted polyalkyl[meth]acrylate still containing the original short-chain alkyl groups (i.e., repeating unit A) make up about 0.5 to about 40 mol % of the total number of repeating units. That is, about 60 to about 99.5% of the R groups in the initial polymer containing repeating unit A are substituted with the R' group of the long chain alcohol reactant R'OH to form repeating unit B and ROH. In one embodiment, the substituted polyalkyl[meth]acrylate containing the long-chain alkyl side chain (i.e. repeating unit B) may be about 80 to about 99 mol % of the total number of repeating units in the polymer.

The amount of long-chain alcohol R'OH in the solid product composition is about 0.5 to about 40 mol % relative to the total number n of repeating units in the polymer. That is, the number of R'OH moles present is about 0.05 n to about 0.40 n. In one embodiment, the long-chain alcohol is present as about 1 to about 30 mol %, and in another embodiment is present as about 2 to about 20 mol %, all relative to the number n of repeating units present in the composition.

As discussed in more detail below, the substituted polyalkyl[meth]acrylate/long chain alcohol composition thus created may be employed as an ingredient, such as a thickener, for use in creating a cosmetic or other personal care product, for example. The substituted polyalkyl[meth]acrylate/long chain alcohol composition is generally present as about 0.1 to about 20% by weight in such products and can be used with cosmetic and other personal care products having a cosmetic base media that is selected from the group consisting of cosmetic oil (i.e. oils compatible for cosmetic uses), water, cosmetic solvents (e.g., solvents compatible for cosmetic uses including certain alcohols) and combinations thereof. Examples of suitable cosmetic solvents include at least one member from the group of lower monoalcohols comprising from 1 to 5 carbon atoms, such as ethanol and isopropanol, glycols comprising from 2 to 8 carbon atom, such as propylene glycol, ethylene glycol, 1,3 butylene glycol and dipropylene glycol, C3-4 ketones and C2-C4 aldehydes.

While the substituted polyalkyl[meth]acrylate/long-chain alcohol composition may be particularly suitable as a thickener in a variety of personal care products it may also be used for encapsulation and deposition of certain chemical species for use in personal care. For example, in embodiments in which the long-chain alcohol is behenyl alcohol, a material known for treatment of cold-sores, the substituted polyalkyl[meth]acrylate/long-chain alcohol composition may be added to a personal care product to provide both a thickening functionality as well as to deliver an active ingredient.

Personal care products in which the substituted polyalkyl[meth]acrylate/long-chain alcohol composition may advantageously be used include anhydrous oil-base products, such as certain anhydrous hair care or treatment products (e.g., gels), scalp treatments, sunscreens, antiperspirant deodorants, and color cosmetics (e.g., blush, lipstick, etc.); water-in-oil emulsions, such as certain skin moisturizers, sunscreens and antiperspirant deodorants; oil-in-water emulsions, such as certain skin moisturizers, sunscreens and mousse/hair styling materials; and alcohol and aqueous based products such as certain mascaras, shampoos, coloring shampoos, hair spray products, hair styling products, facial cleansers, body cleansers, liquid hand soaps and other hand cleansers, fragrance and body odor products, all of the foregoing of which are presented by way of example only.

The polyalkyl[meth]acrylate/long-chain alcohol composition can be effective with a broad range of cosmetic oils, such as esters (e.g., alkyl benzoates having between 12 to 15 carbons), triglycerides (e.g., Caprylic/Caprylate triglyceride), hydrocarbons (e.g., mineral oil, sunflower oil), natural oils (e.g., jojoba oil, safflower oil), and castor oil, among others. Suitable oils are also disclosed, for example, at column 3, line 37, to column 4, line 4, of U.S. Pat. No. 5,736,125; hereby incorporated by reference. Silicone oils may also be used as cosmetic oils.

The following are non-limiting examples of anhydrous cosmetic formulations containing thickened oils incorporating substituted polyalkyl[meth]acrylate/long-chain alcohol compositions as described above:

A) Thickened Anhydrous Oils suitable for personal care applications (e.g. hair gels):
  Oils—about 50 to about 95 wt % (about 10 to about 95 wt % for silicone oils)
  Polyalkyl[meth]acrylate/long-chain alcohol—about 1 to about 20 wt %
  Other Additives or Actives—about 0.1 to about 30 wt %
B) Anhydrous Scalp Serum:
  Oils—about 50 to about 95 wt % (about 10 to about 95 wt % for silicone oils)
  Polyalkyl[meth]acrylate/long-chain alcohol—about 1 to about 20 wt %
  Other Additives or Actives—about 0.1 to about 30 wt %
C) Anhydrous Sunscreen Stick or Gel:
  Oils—about 50 to about 95 wt % (about 10 to about 95 wt % for silicone oils)
  Polyalkyl[meth]acrylate/long-chain alcohol—about 1 to about 20 wt %
  Other Additives or Actives—about 0.1 to about 30 wt %
D) Anhydrous Antiperspirant Deodorant Stick or Gel:
  Emollient—about 50 to about 95 wt %
  Polyalkyl[meth]acrylate/long-chain alcohol—about 1 to about 20 wt %
  Antiperspirant deodorant (APDO) actives—about 0.1 to about 30 wt %
  Other Additives or Actives—about 1 to about 30 wt %
E) Color Cosmetic (e.g. blush, lipstick)
  Oil—about 50 to about 95 wt %
  Polyalkyl[meth]acrylate/long-chain alcohol—about 1 to about 20 wt %
  Pigment—about 0.1 to about 30 wt %
  Other Additives or Actives—about 0.1 to about 10 wt %

Some of the polyalkyl[meth]acrylate/long-chain alcohol composition in the anhydrous cosmetic formulations may be replaced with conventional thickeners such as waxes like carnauba wax, bees wax, and Candelilla wax, among others.

Water-in-oil emulsions are typically prepared by mixing together (1) a heated (i.e., melted) solution of the polyalkyl[meth]acrylate/long-chain alcohol composition in any of the previously discussed oils and (2) an aqueous phase, the aqueous phase being at a temperature similar to the oil solution (typically within about 10° C.); and then cooling the mixture while stirring. The ratio of the aqueous phase to the oil phase can be, for example, about 0.5:1 to about 9:1.

The following are non-limiting examples of cosmetic formulations comprising water-in-oil emulsions:
A) Skin Moisturizer
  Water—about 50 to about 90 wt %
  Silicone—about 1 to about 10 wt %
  Emulsifier—about 0.5 to about 5 wt %
  Emollient—about 5 to about 20 wt %
  Polyalkyl[meth]acrylate/long-chain alcohol—about 0.5 to about 3 wt %
  Other Additives or Actives—about 0.1 to about 3 wt %
B) Sunscreen
  Water—about 50 to about 90 wt %
  Silicone—about 1 to about 10 wt %
  Emulsifier—about 0.5 to about 5 wt %
  Emollient—about 5 to about 20 wt %
  Polyalkyl[meth]acrylate/long-chain alcohol—about 0.5 to about 3 wt %
  Sunscreen Active—about 1 to about 25 wt %
  Other Additives or Actives—about 0.1 to about 3 wt %
C) Antiperspirant Deodorant
  Water—about 50 to about 90 wt %
  Silicone—about 1 to about 10 wt %
  Emulsifier—about 0.5 to about 5 wt %
  Emollient—about 1 to about 20 wt %
  Polyalkyl[meth]acrylate/long-chain alcohol—about 0.5 to about 6 wt %
  APDO actives—about 0.1 to about 30 wt %
  Other Additives or Actives—about 0.1 to about 5 wt %

Oil-in-water emulsions are prepared by mixing together (1) a heated (i.e., melted) solution of the polyalkyl[meth]acrylate/long-chain alcohol composition in the oil phase and (2) an aqueous phase, the aqueous phase being at a temperature similar to the emollient solution (typically within about 10° C.); and then cooling the mixture while stirring. The ratio of the oil phase to the water phase can be, for example, about 0.1:1 to about 1:1. The following are non-limiting examples of cosmetic formulations comprising oil-in-water emulsions:
A) Skin Moisturizer
  Water—about 50 to about 90 wt %
  Emulsifier—about 0.5 to about 5 wt %
  Emollient—about 1 to about 20 wt %

Polyalkyl[meth]acrylate/long-chain alcohol—about 0.5 to about 3 wt %
Other Additives or Actives—about 0.1 to about 3 wt %
B) Sunscreen
    Water—about 50 to about 90 wt %
    Emulsifier—about 0.5 to about 5 wt %
    Emollient—about 1 to about 20 wt %
    Polyalkyl[meth]acrylate/long-chain alcohol—about 0.5 to about 3 wt %
    Sunscreen Active—about 1 to about 25 wt %
    Other Additives or Actives—about 0.1 to about 3 wt %
C) Mousse or other hair styling product
    Water—about 50 to about 90 wt %
    Emulsifier—about 0.5 to about 1 wt %
    Surfactant—about 0.1 to about 2 wt %
    Polyalkyl[meth]acrylate/long-chain alcohol—about 0.5 to about 1 wt %
    Other Additives or Actives—about 0.1 to about 2 wt %
    Solvent—about 1 to about 25 wt %
    Propellant—about 6 to about 10 wt %

As briefly described previously, the polyalkyl[meth]acrylate/long-chain alcohol can also be used with alcohol or aqueous systems, for example, as a thickener as well as to provide benefits of film forming, controlled delivery or deposition of actives, and fragrance or volatiles retention. The following are non-limiting examples of cosmetic formulations comprising alcohol or aqueous systems.

A) Coloring Shampoo
    Water—about 50 to about 90 wt %
    Surfactant—about 2 to about 20 wt %
    Foam booster—up to about 20 wt %
    Polyalkyl[meth]acrylate/long-chain alcohol—about 0.5 to about 5 wt %
    Other Additives or Actives—about 0.1 to about 10 wt %
B) Hair Spray (aerosol and non-aerosol)
    Water—about 10 to about 90 wt %
    Polyalkyl[meth]acrylate/long-chain alcohol—about 0.5 to about 5 wt %
    Ethanol or other solvents—about 33 to about 90 wt %
    Optional Propellant for an aerosol—about 0 to about 50 wt %
    Other Additives or Actives—about 0.1 to about 2 wt %
C) Shampoo
    Water—about 50 to about 90 wt %
    Surfactant—up to about 20 wt %
    Foam booster—about 2 to about 20 wt %
    Polyalkyl[meth]acrylate/long-chain alcohol—about 0.1 to about 2 wt %
    Other Additives or Actives—about 0.1 to about 10 wt %
D) Hair Styling products
    Water—about 10 to about 90 wt %
    Polyalkyl[meth]acrylate/long-chain alcohol—about 0.5 to about 5 wt %
    Ethanol or other solvents—about 0 to about 10 wt %
    Other Additives or Actives—about 0.1 to about 10 wt %
E) Body cleansing products
    Water—about 50 to about 90 wt %
    Surfactant—about 2 to about 20 wt %
    Polyalkyl[meth]acrylate/long-chain alcohol—about 0.5 to about 5 wt %
    Foam booster—up to about 20 wt %
    Other Additives or Actives—about 0.1 to about 10 wt %.

In products in which emollients are employed, any suitable emollient for use in cosmetic compositions can be used. Examples of suitable emollients include esters (e.g., C12-15 alkyl benzoate) and triglycerides (e.g., Caprylic/caprylate triglyceride); hydrocarbon oils (e.g., mineral oil), natural oil (e.g., Jojoba oil, safflower oil), tridecyl trimellitate, sunflower oil, castor oil, among other compounds used to impart improved sensory or aesthetic properties of a personal care composition.

In products in which emulsifiers are employed, any suitable cosmetic emulsifier having a hydrophilic-lipophilic balance (HLB) in the range of 1 to 20 can be used. Examples of suitable emulsifiers include glyceryl stearate, PEG-150 distearate, glyceryl dilaurate, PEG-20 stearate, cetearyl alcohol and ceteareth-20, and PEG-30 Dipolyhydroxystearate.

If desired, one or more properties of a cosmetic composition can be controlled by adding a plasticizing compound to the composition. Examples of such additive compounds referenced above include one or more members selected from the group consisting of silicone based plasticizers, natural or synthetic compounds (e.g., polysaccharides, natural or synthetic gums, stabilizers, anionic and nonionic associative thickener or rheology modifiers soluble in oil or water phase), other film forming polymers like polyurethanes, pyrrolidines (e.g., polyvinylpyrrolidine), among other compounds. The additives may include a compound selected from the group consisting of preservatives, stabilizers (e.g., Xanthan Gum), humectants (e.g., MP Diol, Sorbitol, and Hexylene Glycol), antioxidant (e.g., Vitamins), rheology modifiers, fragrances, and pigments, among other additives.

Surfactants and/or foam boosters may also be employed. While any suitable surfactant and/or foam booster can be employed, examples include members selected from the group consisting of sodium laureth sulfate, sodium lauryl sulfate, ammonium laureth sulfate, ammonium lauryl sulfate, and cocamidopropyl betaine.

In products in which propellant or solvents are employed, those may include isobutene, butane, dimethyl ether, and ethanol, among others.

In some personal care products, active compounds that interact with or protect skin or hair can be included. Examples of such active compounds include sunscreen compounds (e.g. zinc oxide, titanium dioxide, octinoxate, octocrylene, ethylhexyl Salicylate, oxybenzone); skin whitener (e.g. salicylic acid); anti-cellulite compounds; anti-aging compounds (e.g., polypeptides such as Argininie/Lysine, Argininie PCA, *Aspergillus/Aspidosperma Quebracho* Ferment, *Avena Sativa* (Oat) Kernel Protein, and Avocado Sterols, proteins, peptides, copper peptides, fermented biopolymers, beta-glucan, botanical actives, Bifida Ferment Lysate, *Calophyllum Inorhylum* seed oil, *camellia sinensis* extract, ceramides, *chlorella vulgaris* extract, *coriolus versicolor* extract, *corylus avellana* (hazel) seed extract, Hyaluronic acid, Hydrolyzed elastins, Hydrolyzed proteins, Hydrolyzed soy flour, Hydrolyzed peptides, and Vitamins A, E, C, K, and B5 as well as Niacinamide); APDO compounds (e.g., aluminum chlorohydrate, aluminum zirconium tetra chlorohydrex); vitamins (e.g., Tocopherol natural, Synthetic Tocopherol, Synthetic tocopherol acetate, Retinol, Retinyl palmitate, acetate, Provitamin B-5, Ascorbic acid, Sodium ascorbyl phosphate, Ascorbyl glucoside, Magnesium ascorbyl phosphate); Polysaccharides (e.g., Hyaluronic acid, B-1,3-glucans, Chitosan); Botanicals (e.g., Aloe vera, Green tea extract, Grape seed extract, Isoflavones, Chamomille/bisabolol, Fennel, Ginko, Ginseng, Guava); Alpha Hydroxy Acids (e.g., Citric acid, Glycolic acid, Lactic acid); Sugar cane extracts; insect repellents; and Coenzymes and Enzymes (e.g., Ubiquinone, Coenzyme Q10), all by way of example only.

EXAMPLES

The invention is further described by way of the following examples, which are presented by way of illustration, not of limitation.

Example 1

Excess poly(methyl acrylate) homopolymer having a weight average molecular weight of about 40,000 g/mol was reacted with behenyl alcohol in a 1:0.9 molar ratio (methyl acrylate repeating units:behenyl alcohol). A solution of 4.3 g poly(methyl acrylate) in 10.75 mL toluene was initially prepared, to which an additional 50 mL of toluene was then added. The diluted solution was placed in a 3-neck 250 mL round bottom flask, along with 14.65 g behenyl alcohol (44.86 mmol) and 30 mg of sodium methoxide as a catalyst.

The flask was equipped with a condenser and Dean-Stark trap, glass stopper and septum and an atmosphere of nitrogen was introduced to the flask. The reaction mixture in the flask was then heated to reflux. At 30 minute intervals, 10 mL of solvent (containing toluene as well as methanol by-product) was removed and replaced by an equal volume of fresh toluene. Additional 30 mg amounts of sodium methoxide were added at each of 1, 4 and 4.5 hours. After 7 hours of reflux, the mixture was cooled to room temperature. The remaining solvent was removed by vacuum distillation to obtain a solid product of behenyl alcohol and a polyalkyl[meth]acrylate co-polymer containing methyl acrylate and behenyl acrylate repeating units.

Example 2

A second example was prepared using the same poly(methyl acrylate) and behenyl alcohol reagents, in which the methyl acrylate repeating units of the polymer were this time reacted with a stoichiometric equivalent of behenyl alcohol (i.e., 1:1 molar ratio). Again a solution of 4.3 grams of poly (methyl acrylate) in 10/5 mL of toluene was diluted with another 50 mL of toluene. To achieve the desired stoichiometry, the diluted solution was treated with 16.3 g behenyl alcohol (49.84 mmol), still using 30 mg of sodium methoxide as a catalyst. The experiment was otherwise conducted in an identical fashion as in Example 1, such that again after 7 hours of reflux the mixture was cooled to room temperature, the remaining solvent removed by vacuum distillation, and a solid product again obtained of behenyl alcohol and a polyalkyl[meth]acrylate co-polymer containing methyl acrylate and behenyl acrylate repeating units.

Example 3

In a third example, the same reagents were employed in which the poly(methyl acrylate) was reacted in excess behenyl alcohol in a 1:1.1 molar ratio. In this experiment, 17.91 g of behenyl alcohol (54.85 mmol) was used, while everything else was conducted according to the process described in Examples 1 and 2.

The composition of the three samples were confirmed by $^1$H NMR (CDCl$_3$) recorded with a Brucker 300 MHz instrument, which was also used to determine the molar ratio of the three constituents present in the compositions. Molar ratios were calculated from the integration of signals for $CH_2$ in —COOCH$_2$— of the behenyl ester in the substituted repeating units of the polymer, $CH_3$ in —COOCH$_3$ of the methyl ester in the unsubstituted repeating units of the polymer, and the $CH_2$ of OCHCH$_2$— in the behenyl alcohol.

The samples obtained from each of the three experiments, along with a sample of Intelimer IPA 13-6, available from Air Products and Chemicals, Inc., were further analyzed to determine the average molecular weight, viscosity and crystalline melting temperature. The average molecular weight of the experimental and comparative compositions was determined as a weight average by gel permeation chromatography (GPC) using a Waters Alliance 2795 instrument with a refractive index detector. Viscosity of the experimental and comparative compositions was determined at 95° C. using a TA Instruments RDA-III rheometer. Crystallization melting temperature was calculated according to differential scanning calorimetry (DSC) using a TA Universal Analysis instrument with a 10° C. ramp rate using a 10 to 15 mg sample of the experimental and comparative compositions. The results of the analysis are shown below in Table 1.

TABLE 1

| Example No. | Sample Composition (molar ratio) - behenyl acrylate repeating units:methyl acrylate repeating units:behenyl alcohol | Average M. Wt. (weight avg.) | Viscosity (Cp) | DSC Melting Temp. (° C.) |
|---|---|---|---|---|
| 1 | 75:25:13 | 61,131 | 1,035 | 64.66 |
| 2 | 77:23:20 | 60,004 | 424 | 67.15 |
| 3 | 90:10:20 | 59,901 | 1,595 | 68.51 |
| IPA 13-6 (comparative) | 100:0:0 | 106,346 | 513 | 65.73 |

Samples of the substituted polyalkyl[meth]acrylate copolymer/behenyl alcohol composition prepared in examples 1-3 were subsequently dissolved in mineral oil and heated to evaluate their effectiveness for use as an oil thickener. 5 grams of each sample was added to 95 g of USP grade mineral oil and heated to 85° C., about 15 to 20° C. above the samples' crystalline melting points. After cooling, thickening effectiveness (based on a measurement of initial viscosity) were compared to a formulation that used IPA 13-6, a standard poly(behenyl acrylate) homopolymer prepared by a free radical process from its vinyl monomer, in mineral oil at the same 5/95 weight ratio. The viscosity of all four of the compositions in oil were analyzed by a Brookfield viscometer at 10 rpm using a D or F spindle as identified in Table 2. Sensory feel of the formulation was also evaluated with respect to that of neat mineral oil; all had a silky feel and slip.

TABLE 2

| Example | Formulation (g sample/g mineral oil) | Viscosity (Cp) | Spindle Type | Sensory Feel |
|---|---|---|---|---|
| 1 | 5/95 | 607,333 | F | slightly heavier |
| 2 | 5/95 | 158,667 | D | slightly lighter |
| 3 | 5/95 | 153,333 | D | slightly lighter |
| IPA 13-6 (comparative) | 5/95 | 348,333 | F | slightly lighter |

Example 4

In a fourth example, poly(methyl acrylate) is reacted with stearyl alcohol in a 1:1 molar ratio. A solution of 4.3 grams of poly(methyl acrylate) in 10.75 mL of toluene is diluted with another 50 mL of toluene. To achieve the desired stoichiometry, the diluted solution is treated with 13.48 g stearyl alcohol (49.84 mmol), still using 30 mg of sodium methoxide as a catalyst. The experiment is otherwise conducted in an identical fashion as in Example 1, such that again after 7 hours of reflux the mixture is cooled to room temperature and the remaining solvent is removed by vacuum distillation. A solid product is obtained of stearyl alcohol and polyalkyl[meth]acrylate co-polymer containing methyl acrylate and stearyl acrylate repeating units.

Example 5

An oil-in-water emulsion is prepared using the ingredients and weight percentages shown in Table 3. The oil phase ingredients are mixed together in a first vessel and heated to 75° C. The aqueous phase ingredients are separately mixed together in another vessel and also heated to 75° C. The oil phase is then added to the aqueous phase and the emulsion is homogenized for three minutes. A small amount of triethanolamine diluted in water is added to adjust the pH to 5.5.

TABLE 3

|  | Wt. % Total Mixture |
|---|---|
| Aqueous Phase | |
| Deionized Water | Balance |
| Glycerin | 4 |
| DMDM Hydratonin | 0.5 |
| Oil Phase | |
| Mineral Oil (USP grade) | 5 |
| Substituted Polyacrylate/Alcohol (Example 4) | 2 |
| PPG-15 stearyl ether (Arlamol E) | 9 |
| Steareth-21 (Brij S721) | 2.5 |
| Steareth-2 (Brij S2) | 1.1 |
| Cetearyl Alcohol (Crodacol C50) | 4 |
| Dimethicone (DC 200/50 cst) | 2.5 |

Example 6

A water-in-oil emulsion is prepared in the same manner described with respect to Example 5 using the ingredients and weight percentages reflected in Table 4. As in Example 5, a small amount of triethanolamine diluted in water is added to adjust the pH to 5.5.

TABLE 4

|  | Wt. % Total Mixture |
|---|---|
| Oil Phase | |
| Cyclopentasiloxane (SF1202) | 11.5 |
| Isopropyl Palmitate | 4.0 |
| Isopropyl Myristate | 4.0 |
| Mineral Oil (USP grade) | 1.0 |
| PEG-30 Dipoly Hydroxy 'Stearate (Arlacel P135) | 0.5 |
| Bis-PEG/PPG-14/14 Dimethicone (Abil EM 97) | 2.0 |
| Substituted Polyacrylate/Alcohol (Example 4) | 1.0 |

TABLE 4-continued

|  | Wt. % Total Mixture |
|---|---|
| Aqueous Phase | |
| Deionized Water | Balance |
| Magnesium Sulfate | 0.5 |
| Glycerin | 5.0 |
| Mixture of Propylene Glycol, Diazolidinyl Urea, Methylparaben and Propylparaben (Germaben II) | 1 |

Example 7

A water-in-silicone oil emulsion is prepared as in Example 6 using the ingredients reflected in Table 5 below, except that no triethanolamine is used.

TABLE 5

|  | Wt. % Total Mixture |
|---|---|
| Aqueous Phase | |
| Deionized Water | Balance |
| Butylene Glycol | 4.0 |
| Propylene Glycol | 1.0 |
| DMDM Hydratonin | 0.5 |
| Oil Phase | |
| Substituted Polyacrylate/Alcohol (Example 4) | 1.0 |
| Silicone surfactant (DC 5225C) | 10.0 |
| Cyclopentasiloxane (SF 1202) | 16.0 |
| C12-15 alkyl benzoate (Finsole TN) | 0.5 |

Example 8

An anhydrous antiperspirant solid stick is prepared by combining the ingredients reflected in Table 6 below. The ingredients are combined in a vessel in the order listed while the vessel contents are being stirred. The mixture is heated to between about 75 to 80° C. and stirred continuously until all ingredients are completely dispersed and uniform. Once the mixture is uniform, the heat is removed and stirring continues. When the mixture has cooled to between 70 and 72° C., the batch is poured into a mold to form the stick.

TABLE 6

|  | Wt. % Total Mixture |
|---|---|
| PPG-14 Butyl ether | 13.9 |
| Myristyl Myristate | 2.3 |
| Hydrogenated castor oil | 4.0 |
| Stearyl alcohol | 6.0 |
| C12-15 alkyl benzoate | 5.3 |
| Cyclopentasiloxane | 39.5 |
| Substituted Polyacrylate/Alcohol (Example 2) | 5.0 |
| Fumed Silica | 3.0 |
| Aluminum zirconium Pentachlorohydrex Gly | 20.0 |
| Corn Starch | 1.0 |

The invention has been described with reference to certain aspects, but other aspects and embodiments are apparent to persons of skill in the art, and are included within the scope of the claims.

The invention claimed is:

1. A composition comprising:
an alcohol having the composition R'OH; and
a polyalkyl[meth]acrylate having a repeating unit:

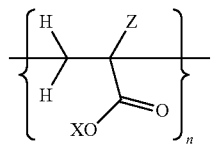

wherein
Z is hydrogen or a methyl group,
X, independently for each repeating unit, is R or R',
R is an alkyl group having 1 to 8 carbon atoms,
R' is an alkyl group having 10 to 30 carbon atoms, and
n is an integer such that the composition has a weight average molecular weight in the range of about 10,000 to about 250,000 g/mol,
wherein repeating units of the polyalkyl[meth]acrylate in which X is R' make up about 60 to about 99.5 mol % of the total number of repeating units n and repeating units of the polyalkyl[meth]acrylate in which X is R make up about 0.5 to about 40 mol % of the total number of repeating units n, and
wherein R'OH is present in the range of about 0.5 to about 40 mol % relative to the total number of repeating units n.

2. The composition of claim 1, wherein R is a straight chain alkyl group having 1 to 4 carbon atoms.

3. The composition of claim 1, wherein R' is a straight chain alkyl group having 16 to 22 carbon atoms.

4. The composition of claim 1, wherein R' is a stearyl or behenyl group.

5. The composition of claim 1, wherein the alcohol is about 0.5 to about 20 mol % relative to the total number of repeating units n, the repeating units in which X is R' are about 80 to about 99.5 mol % of the total number of repeating units n, and the repeating units in which X is R are about 0.5 to about 20 mol % of the of the total number of repeating units n.

6. The composition of claim 1, wherein R is a straight chain alkyl group having 1 to 4 carbon atoms and R' is a straight chain alkyl group having 16 to 22 carbon atoms.

7. A compositon of claim 1 wherein the substituted polyalkyl[meth]acrylate is a product made by a transesterification process comprising:
(a) reacting an alcohol with a polyalkyl[meth]acrylate having a repeating unit A, optionally in a solvent, in the presence of a catalyst to form a substituted alcohol and a substituted polyalkyl[meth]acrylate having a repeating unit B according to the following reaction scheme:

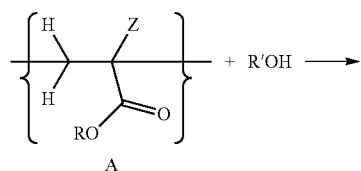

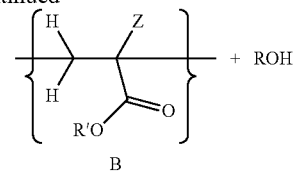

wherein
Z is hydrogen or a methyl group,
R is a straight chain alkyl group having 1 to 8 carbon atoms,
R' is a straight chain alkyl group having 10 to 30 carbon atoms, and
(b) removing the substituted alcohol ROH and any solvent from the reaction product to form a composition consisting essentially of the alcohol R'OH and the substituted polyalkyl[meth]acrylate, wherein the composition formed includes a polyalkyl[meth]acrylate in which about 60 to about 99.5 mol % of the repeating units are repeating unit B, about 0.5 to about 40 mol % of the repeating units are repeating unit A, and the alcohol R'OH is present in the range of about 0.5 to about 40 mol % relative to the total number of repeating units A and B, the composition having a weight average molecular weight in the range of about 10,000 to about 250,000 g/mol.

8. The solid solution of claim 7 wherein the solvent comprises at least one member selected from the group consisting of toluene, xylene, decane, diglyme; and acetonitriles.

9. A composition comprising:
an alcohol having the composition R'OH; and
a polyalkyl[meth]acrylate consisiting of the following repeating unit:

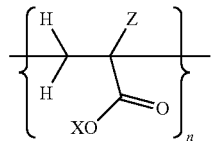

wherein
Z is hydrogen or a methyl group,
X, independently for each repeating unit, is R or R',
R is a straight chain alkyl group having 1 to 4 carbon atoms,
R' is a straight chain alkyl group having 18 or 22 carbon atoms, and
n is an integer such that the composition has a weight average molecular weight in the range of about 40,000 to about 250,000 g/mol,
wherein repeating units of the polyalkyl[meth]acrylate in which X is R' make up about 60 to about 99.5 mol % of the total number of repeating units n and repeating units of the polyalkyl[meth]acrylate in which X is R make up about 0.5 to about 40 mol % of the total number of repeating units n, and
wherein R'OH is present in the range of about 0.5 to about 40 mol % relative to the total number of repeating units n.

10. A personal care product comprising
a cosmetic base media; and
about 0.1% to about 20% by weight of a compound comprising:
an alcohol having the composition R'OH; and
a polyalkyl[meth]acrylate consisting of a repeating unit:

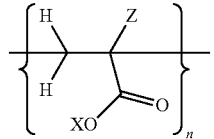

wherein
Z is hydrogen or a methyl group,
X, independently for each repeating unit, is R or R',
R is an alkyl group having 1 to 8 carbon atoms,
R' is an alkyl group having 10 to 30 carbon atoms,
n is an integer such that the compound has a weight average molecular weight in the range of about 10,000 to about 250,000, and
wherein repeating units of the polyalkyl[meth]acrylate in which X is R' make up about 60 to about 99.5 mol % of the total number of repeating units n and repeating units of the polyalkyl[meth]acrylate in which X is R make up about 0.5 to about 40 mol % of the total number of repeating units n, and
wherein R'OH is present in the range of about 0.5 to about 40 mol % relative to the total number of repeating units n.

11. The personal care product of claim 10, wherein the cosmetic media comprises a cosmetic oil.

12. The personal care product of claim 11, wherein the cosmetic oil comprises an oil-base emollient.

13. The personal care product of claim 11, further comprising an emulsifier and water.

14. The personal care product of claim 11, further comprising an emulsifier and water, wherein the personal care product is a water-in-oil emulsion.

15. The personal care product of claim 11, further comprising an emulsifier and water, wherein the personal care product is an oil-in-water emulsion.

16. The personal care product of claim 11, further comprising an active ingredient.

17. The personal care product of claim 10, further comprising a surfactant or foam booster.

18. The personal care product of claim 11, wherein the product is an anhydrous product selected from the group consisting of thickened anhydrous oils, anhydrous hair care products, anhydrous sunscreen, anhydrous antiperspirant deodorants, and color cosmetics.

19. The personal care product of claim 11, wherein the product is a water-in-oil emulsion selected from the group consisting of skin moisturizers, sunscreens, and antiperspirant deodorants.

20. The personal care product of claim 11, wherein the product is an oil-in-water emulsion selected from the group consisting of skin moisturizers, sunscreens, and hair styling products.

21. The personal care product of claim 10, wherein the personal care product is selected from the group consisting of coloring shampoos, hair sprays, shampoos, hair styling products, facial cleaners, body cleansers, fragrances and body odor products.

22. The product of claim 10 further comprising at least one member selected from the group consisting of ethanol, propylene glycol, 1,3 butylene glycol and dipropylene glycol.

23. A solid solution of
an alcohol having the composition R'OH; and
a polyalkyl[meth]acrylate having a repeating unit:

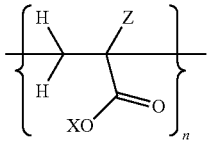

wherein
Z is hydrogen or a methyl group,
X, independently for each repeating unit, is R or R',
R is an alkyl group having 1 to 8 carbon atoms,
R' is a stearyl or behenyl group, and
n is an integer such that the solid solution has a weight average molecular weight in the range of about 10,000 to about 250,000 g/mol,
wherein repeating units of the polyalkyl[meth]acrylate in which X is R' make up about 60 to about 99.5 mol% of the total number of repeating units n and repeating units of the polyalkyl[meth]acrylate in which X is R make up about 0.5 to about 40 mol% of the total number of repeating units n,
wherein R'OH is present in the range of about 0.5 to about 40 mol% relative to the total number of repeating units n; and wherein the solid solution is a solid at room temperature.

24. The solid dolution of claim 23, wherein the polyalkyl [meth]acrylate consists of the repeating unit:

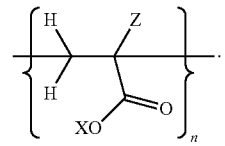

25. The solid solution of claim 23 wherein the solid solution has a crystalline melting point of about 65 to about 70 C.

26. The solid solution of claim 23 further comprising a transesterification catalyst.

27. The solid solution of claim 26 wherein the catalyst comprises at least one member selected from the group consisting of mineral acids, and sulfonic acids, fluoroacids.

28. The solid solution of claim 26 wherein the catalyst comprises a solid acid.

29. The solid solution of claim 26 wherein the catalyst comprises at least one member selected from the group consisting of isopropyl and butyl titanates; alkali metal oxides, hydroxides or alkoxides; oxides, alkyls, carboxylates, halides and alkoxides of transition metals.

30. The solid solution of claim 23 made by a transesterification process comprising:
(a) reacting an alcohol with a polyalkyl[meth]acrylate having a repeating unit A, optionally in a solvent, in the presence of a catalyst to form a substituted alcohol and a substituted polyalkyl[meth]acrylate having a repeating unit B according to the following reaction scheme:

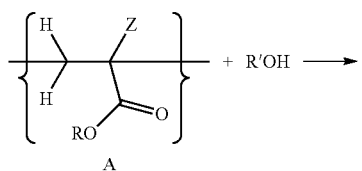

A

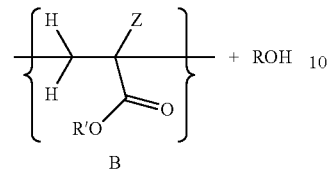

B wherein

Z is hydrogen or a methyl group,

R is a straight chain alkyl group having 1 to 8 carbon atoms,

R' is a straight chain alkyl group having 10 to 30 carbon atoms, and wherein the substituted polyalkyl[meth]acrylate is a random copolymer having repeating units A and B; and (b) removing the substituted alcohol ROH and any solvent from the reaction product to form the solid solution.

31. The solid solution of claim 30 wherein other repeating units of the reactant polyalkyl[meth]acrylate having a repeating unit A does not include functional groups that react during the transesterification process.

32. The solid solution of claim 26 wherein the transesterification catalyst comprises at least one member selected from the group consisting of mineral acids; sulfonic acid catalysts represented by the formula R"SO$_3$H, where R" is a hydrocarbyl group of about 1 to about 25 carbon atoms; zeolites; isopropyl and butyl titanates; alkali metal alkoxides; and alkoxides of transition metals.

33. A composition comprising:

i) a solid solution of an alcohol having the composition R'OH; and a polyalky[meth]acrylate having a repeating unit:

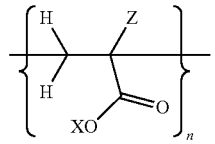

wherein

Z is hydrogen or a methyl group,

X, independently for each repeating unit, is R or R',

R is an alkyl group having 1 to 8 carbon atoms,

R' is an alkyl group having 10 to 30 carbon atoms, and n is an integer such that the solid solution has a weight average molecular weight in the range of about 10,000 to about 250,000 g/mol; and ii) at least one member selected from the group consisting of mineral acids; sulfonic acid catalysts represented by the formula R"SO$_3$H, where R" is a hydrocarbyl group of about 1 to about 25 carbon atoms; and alkali metal alkoxides.

34. The composition of claim 33 wherein the member is selected from the group consisting of sulfonic acid catalysts represented by the formula R"SO$_3$H, where R" is a hydrocarbyl group of about 1 to about 25 carbon atoms; and alkali metal alkoxides.

* * * * *